United States Patent
Alqahtani et al.

(10) Patent No.: US 10,420,731 B1
(45) Date of Patent: Sep. 24, 2019

(54) METHOD OF SYNTHESIZING LIGNIN-BASED NANOCOMPOSITIONS

(71) Applicant: KING SAUD UNIVERSITY, Riyadh (SA)

(72) Inventors: Mohammed Saeed A. Alqahtani, Riyadh (SA); Ali Saeed Althabit Alqahtani, Riyadh (SA); Rabbani Syed S. Baji, Riyadh (SA)

(73) Assignee: King Saud University, Riyadh (SA)

( * ) Notice: Subject to any disclaimer, the term of this patent is extended or adjusted under 35 U.S.C. 154(b) by 0 days.

(21) Appl. No.: 16/252,351

(22) Filed: Jan. 18, 2019

(51) Int. Cl.
| | |
|---|---|
| A61K 9/51 | (2006.01) |
| A61K 36/9066 | (2006.01) |
| B82Y 40/00 | (2011.01) |
| B82Y 5/00 | (2011.01) |

(52) U.S. Cl.
CPC ......... *A61K 9/5192* (2013.01); *A61K 9/513* (2013.01); *A61K 36/9066* (2013.01); *B82Y 5/00* (2013.01); *B82Y 40/00* (2013.01)

(58) Field of Classification Search
None
See application file for complete search history.

(56) References Cited

U.S. PATENT DOCUMENTS

| | | | |
|---|---|---|---|
| 9,233,110 B2* | 1/2016 | Perumal | A61K 31/07 |
| 2003/0013612 A1* | 1/2003 | Asrar | A01N 25/08 |
| | | | 504/359 |
| 2003/0211072 A1 | 11/2003 | Carreno-Gomez et al. | |
| 2014/0329913 A1* | 11/2014 | Hanes | A61K 9/0036 |
| | | | 514/772.1 |
| 2019/0037837 A1* | 2/2019 | Wurm | A01N 25/10 |

FOREIGN PATENT DOCUMENTS

| | | |
|---|---|---|
| CN | 107537039 A | 1/2018 |
| CN | 107693506 A | 2/2018 |
| CN | 108208834 A | 6/2018 |
| WO | 2017134308 A1 | 8/2017 |

OTHER PUBLICATIONS

Lee, Jung-Bum, et al.; "Antiviral and Immunostimulating Effects of Lignin-Carbohydrate-Protein Complexes from Pimpinella anisum": Bioscience, Biotechnology, and Biochemistry; Mar. 7, 2011; pp. 459-465.

Asina, Fnu, et al.; "Biodegradation of lignin by fungi, bacteria and laccases"; Bioresource Technology 220 (2016); pp. 414-424.

Reddy, Narendra, et al.; "Crosslinking biopolymers for biomedical applications"; Trends in Biotechnology vol, 33 No. 6; Jun. 2015; pp. 362-369.

(Continued)

*Primary Examiner* — Jacob T Minskey
(74) *Attorney, Agent, or Firm* — Richard C. Litman

(57) ABSTRACT

A method of preparing lignin-based nanoparticles includes using a phase separation method, stabilized by citric acid (CA) crosslinking. The compositions include lignin-based nanoparticles (LG NPs) and a drug or pharmaceutical treating agent encapsulated in the LG NPs. A mean particle size diameter of the drug-loaded LG NPs can be less than 100 nm. The LG NPs improve oral bioavailability, and achieves rapid absorption of the encapsulated drug.

1 Claim, 9 Drawing Sheets

(56) References Cited

OTHER PUBLICATIONS

Vinardell, Maria Pilar, et al.; "Lignins and Their Derivatives with Beneficial Effects on Human Health"; International Journal of Molecular Sciences 2017, 18, 1219.
Naseem, Amina, et al.; "Lignin-derivatives based polymers; blends and composites: A review"; International Journal of Biological Macromolecules 93 (2016); pp. 296-313.
Ten, Elena, et al.; "Recent developments in polymers derived from industrial lignin"; Journal of Applied Polymer Science; 2015.
Liu, Weidong, et al.; "Oral bioavailability of curcumin: problems and advancements" Journal of Drug Targeting vol. 24 No. 8, 2016, pp. 694-702.
Sah, Edel, et al.; "Recent Trends in Preparation of Poly(lactide-co-olycolide) Nanoparticies by Mixing Polymeric Organic Solution with Antisolvent"; Journal of Nanoparticles vol. 2015 Article ID 794601.
Abstract of 'Figueiredo, Patricia, et al., "In vitro evaluation of biodegradable lignin-based nanoparticles for drug delivery and enhanced antiproliferation effect in cancer cells." Biomaterials, vol. 121, Mar. 2017, pp. 97-108'.
Abstract of 'Dai, Lin, et al., "Lignin Nanoparticie as a Novel Green Carrier for the Efficient Delivery of Resveratrol," ACS Sustainable Chem. Eng., Jul. 2017, 5 (9), pp. 8241-8249'.
Abstract of 'Podaralla, Satheesh, et al.; "Synthesis of Novel Biodegradable Methoxy Poly(ethylene glycol)—Zein Micelles for Effective Delivery of Curcumin", Molecular Pharmaceutics 2012 9 (9); pp. 2778-2786'.
Abstract of 'Tang, Huadong, el al.; "Curcumin polymers as anti-cancer conjugates.", Biomaterials. 31(27), pp. 7139-7149.'.

\* cited by examiner

METHOD OF SYNTHESIZING LIGNIN-BASED NANOCOMPOSITIONS

BACKGROUND

1. Field

The disclosure of the present patent application relates to a method of preparation of lignin nanoparticle (LG NP) compositions, and particularly to curcumin-loaded lignin nanocompositions.

2. Description of the Related Art

Nanoparticles prepared from a variety of natural and synthetic polymers have been investigated for use in delivery of various drugs and bioactive compounds. Compared to synthetic polymers, natural polymers have the advantage of being green, easily available, and economical. Various natural polymers such as gum acacia, silk, sodium alginate, chitosan, albumin, and gelatin have been explored for drug delivery applications. In contrast to other natural sources, plant biomaterials composed mainly of cellulose, hemicellulose, and lignin offer distinct advantages.

Lignin is an amorphous phenyl propylene polymer and one of the most abundant biopolymers. Lignin is ecofriendly, renewable, and sterile, and seems to be physiologically benign in humans. Lignin further has the advantage of being natural, renewable, biodegradable, biocompatible, and safe. Lignin has been used in the agricultural, cosmetics, and food industries, in controlled release and coated formulations. It has been used also to stabilize emulsions, and has been shown to exhibit surface active properties. Lignin exhibits many health benefits, such as low cytotoxicity; antioxidant activity; antimicrobial activity; and low proinflammatory responses. Lignin is non-hemolytic, and has been shown to be biocompatible with biological cells.

Unlike proteins, lignin evades immune and adverse tissue reactions, making lignin less immunogenic. Lignin films have been shown to provide a better barrier due to lignin's unique chemical structure and mechanical strength, as well as its water and oxygen impermeability. In addition, lignin includes aromatic and aliphatic hydroxyl groups in its chemical structure, enabling further chemical modifications or ligand attachments.

Curcumin, the curcuminoid extract and the active diferuloylmethane compound of *Curcuma longa* (in the ginger family Zingiberaceae—containing species such as turmeric and Siam Tulip), has been generally recognized as safe (GRAS) by the United States Food and Drug Administration (FDA). Curcumin is reported to be very hydrophobic compound (log P 3.7) with poor water solubility (less than 1 μg/mL). Curcumin can modulate various signaling pathways, such as COX-2, protein kinase C, glutathione, MMPs, ATPase and others, demonstrating a wide range of medicinal benefits such as antimalarial, antibacterial, antiviral, antiinflammatory, anti-rheumatic, anti-diabetic, anti-oxidant, anti-cancer and chemo-preventive properties. In particular, due to the stability issues of most CUR medications, the development of a suitable CUR oral dosage form is difficult—most available formulations suffer from poor stability and burst release, and many contain unsafe excipients. An oral CUR formulation that provides sustained release is desirable to provide a higher efficacy, increasing the short plasma concentration half-life, reducing the administration frequency, and reducing the incidence and severity of side effects caused by the drug.

Poor water solubility, chemical instability, and extensive gut metabolism contribute to poor oral bioavailability for curcumin. In addition, low bioavailability of curcumin is related to poor membrane permeability, and the influence of the efflux pump of permeability glycoprotein/Multidrug Resistance-associated Protein 2 (P-gp/MRP2) in intestinal epithelial cells. Accordingly, curcumin, and in particular the successful oral delivery of curcumin and similar treating agents, has particular interest in the pharmaceutical industry.

Thus, a method of synthesizing lignin-based nanocompositions solving the aforementioned problems is desired.

SUMMARY

A method of preparing lignin-based nanocompositions includes using a phase separation method, stabilized by citric acid (CA) crosslinking. The nanocompositions include lignin-based nanoparticles (LG NPs) and a drug or pharmaceutical treating agent encapsulated in the LG NPs. As such, the LG NPs can be used as an oral drug delivery system. A mean particle size diameter of the drug-loaded LG NPs can be less than 100 nm. The LG NPs improve oral bioavailability, and achieves rapid absorption of the drug encapsulated within the LG NPs. The encapsulation efficiency of CUR in the nanoparticles can be about 92%. The drug can be a model Biopharmaceutical Classification System (BCS) Class IV compound, such as curcumin (CUR).

These and other features of the present method will become readily apparent upon further review of the following specification.

DETAILED DESCRIPTION OF THE PREFERRED EMBODIMENTS

Figure 1A:
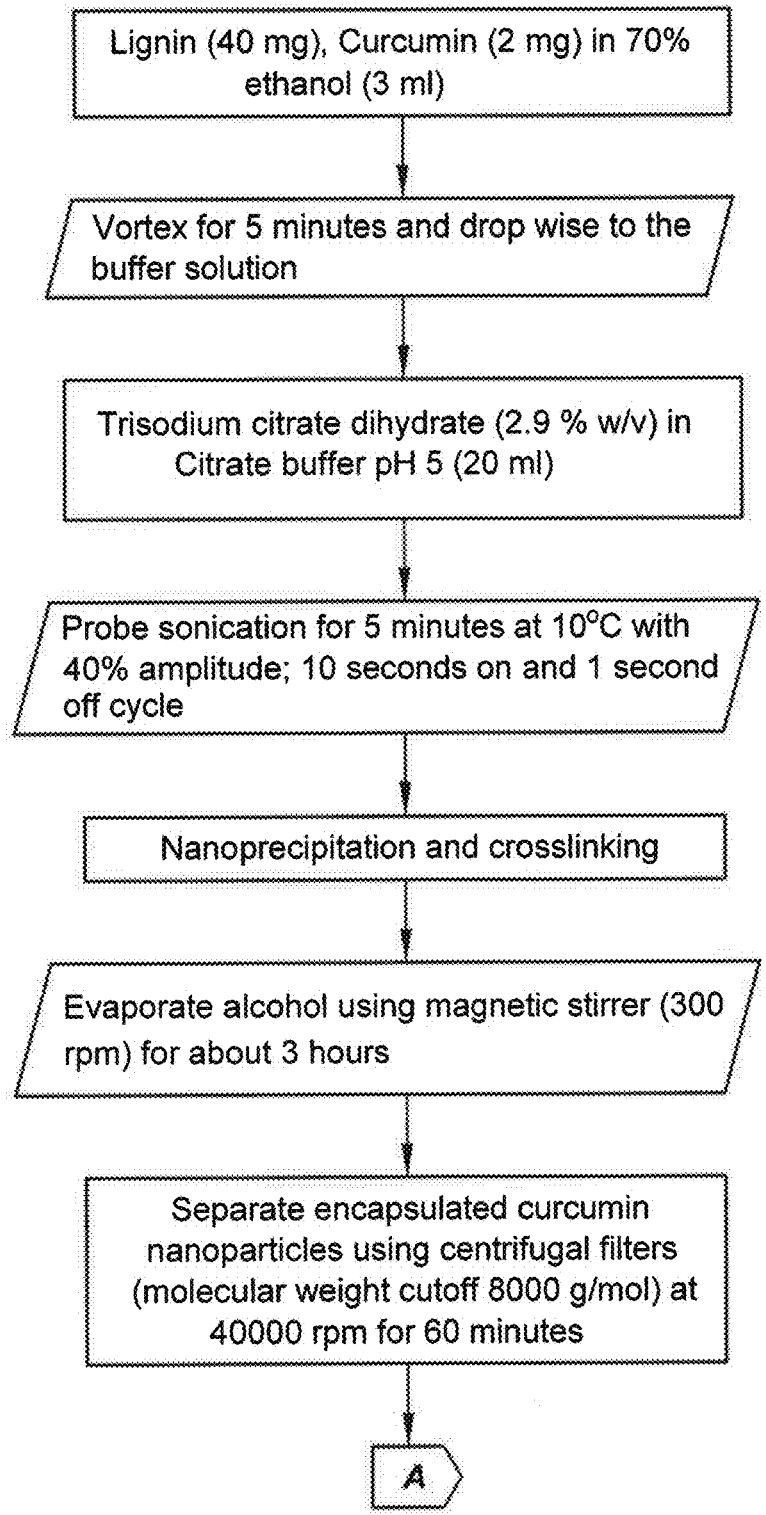
FIG. 1A is a flow chart illustrating the initial steps of preparation of the nanocompositions using the emulsion solvent evaporation method detailed below.

A method of preparing lignin-based nanocompositions includes using a phase separation method, stabilized by citric acid (CA) crosslinking. The nanocompositions include lignin-based nanoparticles (LG NPs) and a drug or pharmaceutical treating agent encapsulated in the LG NPs. The method can include dissolving lignin in a solvent including alcohol and a pharmaceutical treating agent to form an alcoholic phase, adding the alcoholic phase to an aqueous phase including a citrate buffer to form a colloidal dispersion, and evaporating the alcohol from the colloidal dispersion to prepare a dried formulation including the nanocompositions. A mean particle size diameter of the drug-loaded LG NP composition or nanocomposition can be less than 100 nm. The LG NPs improve oral bioavailability and achieves rapid absorption of the drug encapsulated within the LG NPs. The nano-compositions provide enhanced protection of the entrapped drug during storage conditions. Further, as described in detail herein, the nano-compositions provide stability in simulated intestinal fluid, and a desirable slow release under simulated gastric conditions.

According to an embodiment, the particles have a size in the nanometer range, with a narrow polydispersity. In one aspect, the average size of said nanoparticles is between about 50 nm to about 80 nm, e.g., about 80 nm to about 100 nm, about 100 nm to about 120 nm, or about 120 nm to about 200 nm. In another aspect, the nanoparticles exhibit an encapsulation efficiency of about 70% to about 95%, and a loading efficiency of about 1% to about 9%. In a related aspect, the particles exhibit a smooth, spherical surface.

According to an embodiment, the encapsulated drug can be a model Biopharmaceutical Classification System (BCS) Class IV compound, such as curcumin (CUR). Such compounds otherwise provide poor oral bioavailability, according to BCS. For example, Class IV compounds demonstrate low permeability (i.e., low absorption across human intestinal membrane) and low aqueous solubility. Oral delivery of pharmaceutical products is the simplest and the most convenient route of administration. As such, successful CUR therapy requires an appropriate delivery system that enhances oral absorption and bioavailability.

The nanoparticles can improve the stability of the encapsulated drug molecules by protecting them from surrounding pH influence and premature metabolic degradation, while increasing their solubility and promoting sustained release and absorption. The nanoparticles can lower the risk of systemic toxicity, while enhancing drug efficacy, specificity, and tolerability, as well as the therapeutic index. In embodiments, the nanoparticle formulations may be used as an oral controlled drug delivery system for CUR. In a related aspect, the stability of CUR is increased in CUR loaded nanoparticles of the present disclosure. In another aspect, uptake of the nanoparticles may be carried out with the cells in vitro, including but not limited to Caco-2 polarized cells.

Using the Caco-2 cell (i.e., human colon carcinoma cell line) monolayer model, the CUR-loaded LG NPs were tested for cellular uptake and transepithelial permeability. It was found that the loaded LG NPs did not exhibit CUR toxicity on the cells, in contrast to free CUR. The loaded nanoparticles also exhibited enhanced cell uptake and enhanced intestinal permeation compared to free CUR. Incubation of the loaded nanoparticles in the Caco-2 cell monolayer led to a five-fold increase in apparent permeability compared with free CUR. Further, in vivo pharmacokinetics studies confirmed that the oral bioavailability of the curcumin loaded in the nanoparticles was increased by 10-fold compared with free curcumin.

The lignin can be extracted by various methods and from various plant sources. Preferably, the lignin exhibits good solubility in organic solvents and a relatively optimum molecular weight. In an embodiment, organosolv lignin (i.e., lignin that was solubilized by the solvent-based pulping technique known as organosolv) is used to prepare the nano-compositions, e.g., curcumin-loaded lignin nanoparticles (CUR-loaded LG NPs).

Figure 1B:
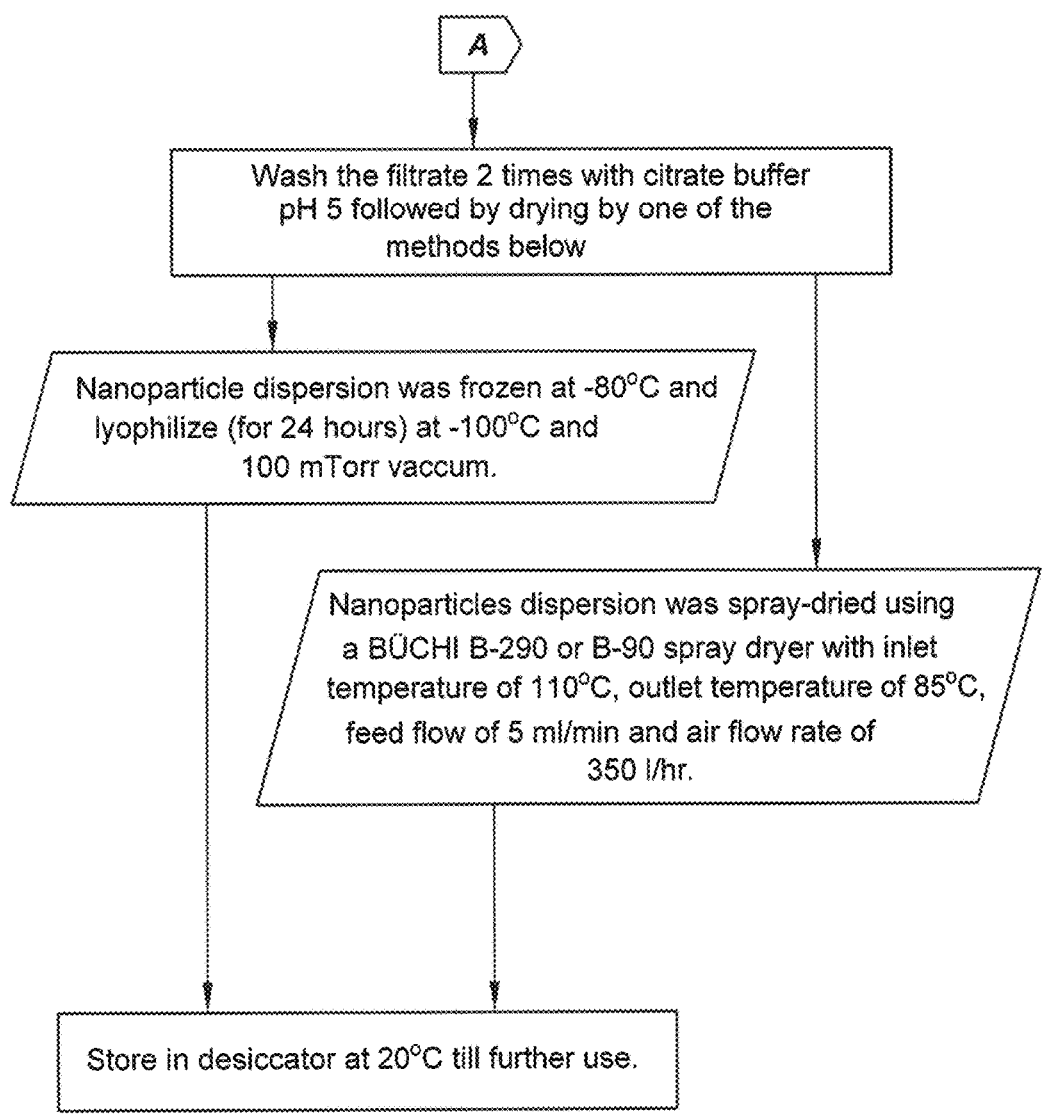
FIG. 1B is a flow chart illustrating the final steps of preparation of the nanocopositions using the emulsion solvent evaporation method detailed below.
Figure 6:
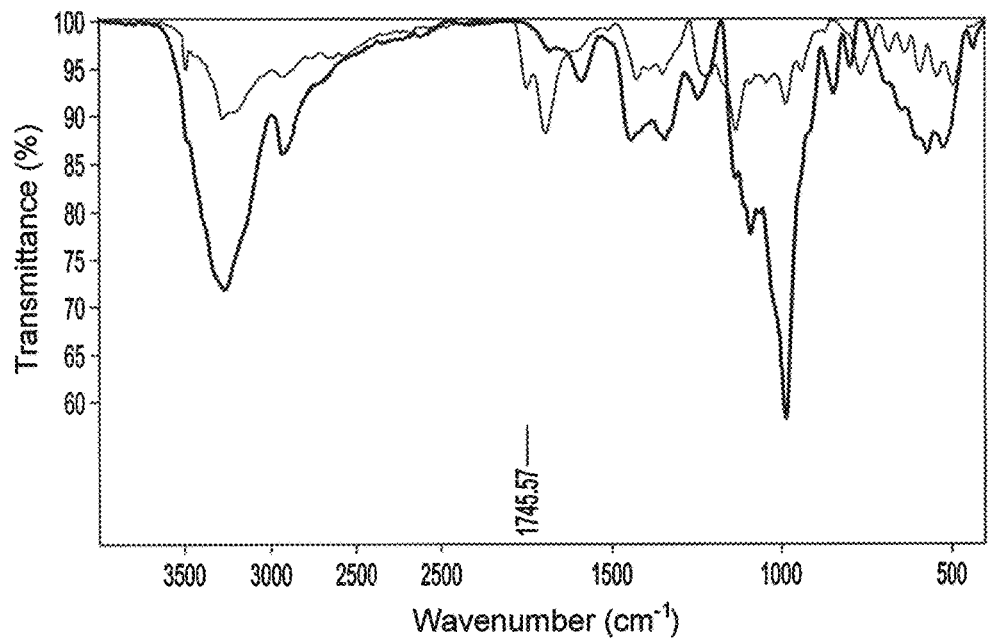
FIG. 6 is a Fourier-transform infrared spectroscopy (FTIR) analysis of lignin powder and CA cross-linked LG NPs.

As shown in FIG. 1, the lignin can be crosslinked using citric acid (CA) as the cross-linker. Citric acid provides polyanions that are able to react with hydroxyl groups found on polysaccharides. The crosslinking method can form a relatively coherent matrix structure of the polymer to entrap the drug of interest. Crosslinking can produce a matrix of enhanced stability and encapsulation that protects and slowly releases the entrapped drug. Fourier-Transform IR spectroscopy (FTIR) confirmed that the cross-linking provides formation of ester linkages between carboxyl groups of the citric acid and hydroxyl groups of lignin (FIG. 6). The FTIR spectra showed the intensity of the band near 3000-3500 cm-1, corresponding to stretching of hydroxyl groups present in raw lignin. As seen in FIG. 6, this is decreased significantly in the crosslinked nanoparticles. In addition, the increased intensity of the band corresponding to the carbonyl ester C=O stretching for the nanoparticles at 1745.5 cm-1 also indicates the presence of esterification crosslinking resulting from the reaction between carboxylic groups of citric acid and hydroxyl groups of lignin. The esterified hydroxyl groups present on the lignin leads to the formation of crosslinks, making the nanoparticle surface more negatively charged and promoting the formation of a stable, less-degradable particle in acidic media.

Table 1 shows the effects of lignin concentration on the particle size and distribution or PDI (polydispersity index).

TABLE 1

Optimization of lignin concentration

| Formulation Code | Lignin Conc. (% w/v) | Particle size (nm) | PDI |
|---|---|---|---|
| LG NPS-1 | 0.1 | 86.4 ± 7.27 | 0.111 ± 0.018 |
| LG NPS-2 | 0.4 | 87.9 ± 8.32 | 0.116 ± 0.015 |
| LG NPS-3 | 0.7 | 108.6 ± 11.23 | 0.228 ± 0.116 |
| LG NPS-4 | 1.0 | 138.7 ± 10.23 | 0.309 ± 0.135 |
| LG NPS-5 | 1.5 | 244.1 ± 28.91 | 0.466 ± 0.142 |

As reflected in Table 1, lignin concentration significantly affects the particle size of the LG NPs. Increased average particle size was associated with increased lignin concentration. A highly significant ($p<0.05$) increase in particle size was associated with PDI above 0.4% lignin concentration. This may be attributed to decreased citric acid accessibility to the polymeric chain due to an increase in the viscosity of the polymeric solution at its higher concentration. From preliminary data, other formulation parameters, such as the CUR ratio, solvent composition, rate of sonication, and temperature, also were optimized.

As shown in Table 2, optimum nano-compositions were found to have a particle size of 85.9±4.7 nm, low PDI, and narrow size distribution.

TABLE 2

Characteristics of blank and curcumin loaded LG NPs

| Particle size (nm) | PDI | Zeta Potential (mV) | Encapsulation efficiency (%) |
|---|---|---|---|
| 85.9 ± 4.7 | 0.121 ± 0.017 | −41 ± 1.5 | — |
| 104 ± 5.3 | 0.125 ± 0.013 | −37 ± 2.6 | 92 ± 4 |

Each value is reported as a mean ± SD; n = 3.

Generally, nano-particles with a particle diameter size less than 300 nm and a hydrophobic surface can provide superior uptake from gastrointestinal tract as compared to other delivery options. Particle sizes of less than 200 nm have been reported to increase drug solubility and permeability through the biological membrane. PDI values of the prepared nanoparticles ranged from 0.105 to 0.121—a range indicative of monodisperse particles. These nanoparticles were stable with high negative zeta potential of −41.

Figure 2:
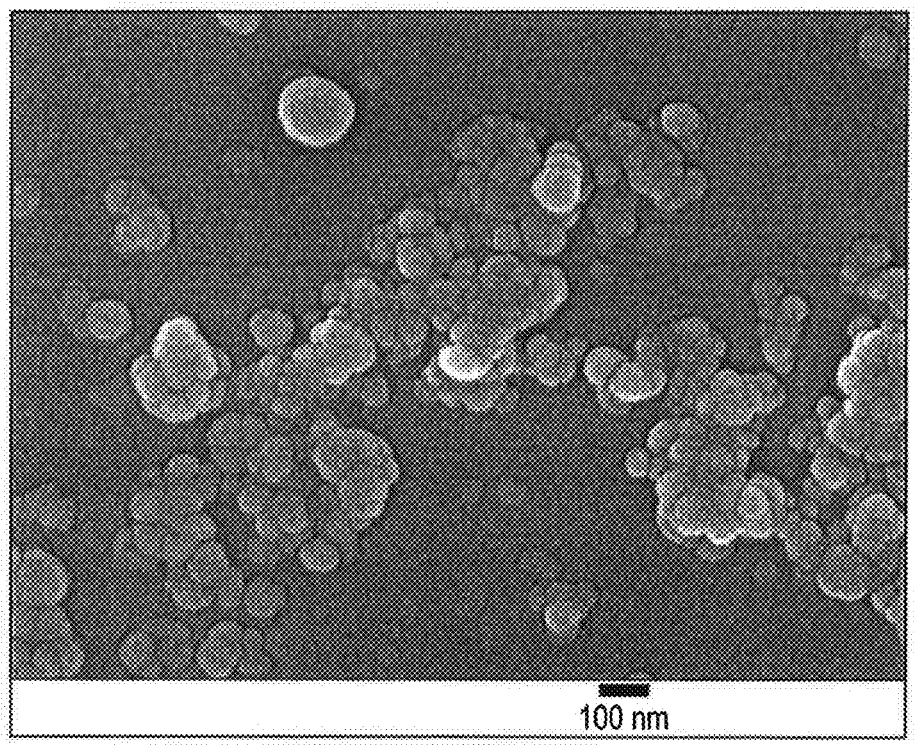
FIG. 2 is a scanning electron microscopy (SEM) image, scale bar 100 nm.
Figure 3:
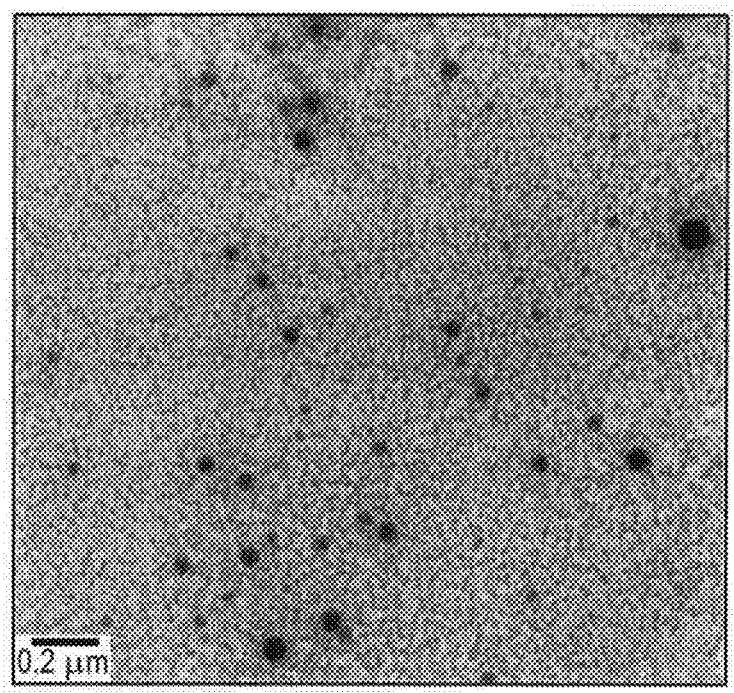
FIG. 3 is a transmission electron microscopic (TEM) image, scale bar 0.2 μm.
Figure 4:
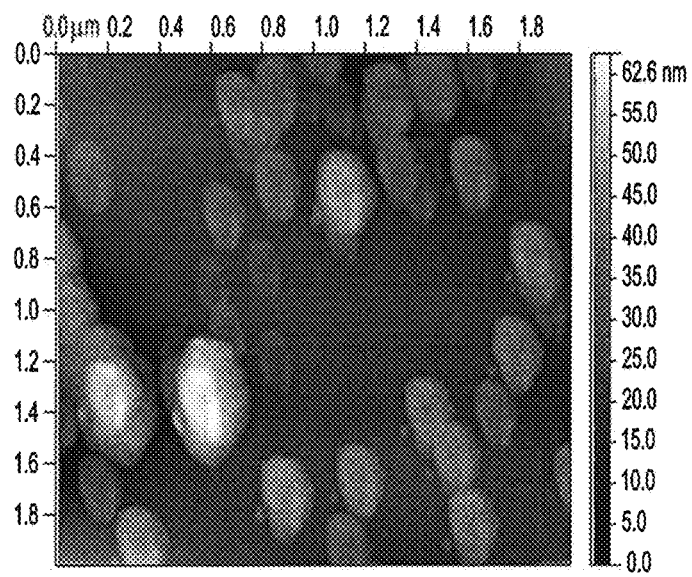
FIG. 4 is a two-dimensional image depicting topography and size distribution of LG NPs, using Atomic Force Microscopy.

As can be seen from Scanning Electron Microscope (SEM) and Transmission Electron Microscope (TEM) images, the LG NPs were spherical with a smooth morphology and a uniform structure (FIGS. 2 and 3). The Atomic Force Microscopy (AFM) image shows the spherical topography of LG NPs (FIG. 4).

The formation of stable and dispersible nanoparticles is important in developing an oral formulation. As shown in Tables 3-4, the LG NPs were found to be stable at a range of pH or ionic strength, with no significant change in particle size and thus no particle aggregation.

TABLE 3

Influence of pH on mean size and polydispersity index of LG NPS

| pH | Particle size (nm) | PDI |
|---|---|---|
| 2 | 116.7 ± 12.03 | 0.110 ± 0.018 |
| 3 | 106.1 ± 10.32 | 0.104 ± 0.015 |
| 4 | 99.7 ± 11.23 | 0.108 ± 0.048 |
| 5 | 91.6 ± 09.23 | 0.103 ± 0.024 |
| 6 | 85.8 ± 08.91 | 0.105 ± 0.019 |
| 7 | 83.5 ± 07.10 | 0.097 ± 0.012 |
| 8 | 82.7 ± 05.31 | 0.093 ± 0.011 |
| 9 | 80.4 ± 07.82 | 0.102 ± 0.016 |

Data are expressed as mean ± SD, n = 3.

TABLE 4

Influence of ionic strength on particle characteristics of LG NPS

| Ionic strength (mM NaCl) | Particle size (nm) | PDI | Zeta potential (mV) |
|---|---|---|---|
| 0 | 82.3 ± 07.10 | 0.108 ± 0.05 | −41.3 ± 3.5 |
| 10 | 85.16 ± 08.72 | 0.085 ± 0.025 | −39.25 ± 4.6 |
| 20 | 93.34 ± 10.55 | 0.105 ± 0.015 | −35.8 ± 3.41 |
| 50 | 91.33 ± 14.30 | 0.109 ± 0.016 | −32.15 ± 2.90 |
| 100 | 83.30 ± 09.54 | 0.112 ± 0.018 | −25.05 ± 3.81 |
| 150 | 92.86 ± 09.56 | 0.108 ± 0.021 | −18.6 ± 5.49 |
| 200 | 91.10 ± 06.36 | 0.092 ± 0.018 | −16.15 ± 4.21 |

Data are expressed as mean ± SD, n = 3.

Figure 5:
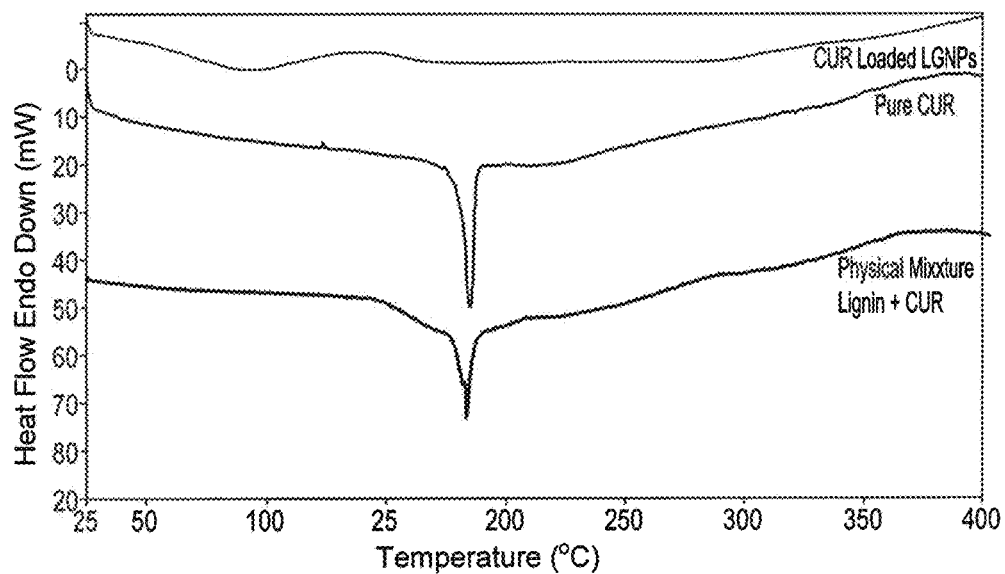
FIG. 5 is a Differential Scanning Calorimetry (DSC) analysis comparing results for pure curcumin; a physical mixture of lignin and curcumin; and curcumin-loaded LG NPs.

Differential Scanning Calorimetry (DSC) was used to determine whether CUR was encapsulated in, or adsorbed on, the LG NPs. The glass transition temperature (Tg) of anhydrous CUR is reported to be about 177.1° C. Experiments conducted by the present inventors revealed CUR having a Tg of about 178° C. both alone and in the physical mixture with lignin (FIG. 5). However, the CUR-loaded LG NPs formulation did not exhibit the melting point of CUR, which indicates that the CUR is molecularly dispersed within the lignin matrix (FIG. 5).

In aqueous solution, curcumin is light-sensitive, degrading with a short half-life at basic pH. To investigate the stability of CUR-loaded LG NPs, the nanoparticles themselves were found to be stable with a minimal increase in mean size (510 nm) after storage at room temperature for 90 days. When CUR was encapsulated in LG NPs, the stability of the curcumin was increased by 100-fold in the presence of light, and by 200-fold in the absence of light. The encapsulation efficiency of CUR was found to be 92±4% with loading efficiency ranging from 2 to 4%.

The lignin-based nanoparticles were shown to improve permeability and oral bioavailability in vitro as well as in vivo. LG NPs possess an optimal size, and high encapsulation efficiency, while exhibiting a sustained pattern of CUR release in the simulated intestinal fluid, and excellent stability in the simulated gastric fluid. The nanoparticles demonstrated increased permeability while eliminating the impact of (P-gp) efflux. Their use provided a significant increase in bioavailability and half-life of the treating agent compared to an oral suspension. The specific in vitro and in vivo results revealed that the effect improved curcumin bioavailability after oral administration. It is thus feasible to encapsulate lipophilic molecules, and possibly other molecules, using the lignin nanoparticles for oral delivery.

The nanoparticles of the present disclosure may be used to treat a variety of diseases including, but not limited to, asthma, COPD, fibrotic lung disease, HIV, cancer, brain tumors, lung tumors, cancers of the blood (e.g., leukemia, myelomas), inflammatory diseases, epilepsy, diabetes, dementia, neurodegenerative disorders, joint disorders, heart disease, infectious diseases, respiratory diseases, hepatic disorders, and autoimmune diseases.

The nanoparticles of the present disclosure can be used in food industry including food processing, food nanosensing, food packaging. The nanoparticles can be used as food additives, carriers for delivery of nutrients, vitamins, anticaking agents, antimicrobial agents, fillers for improving mechanical strength and durability of the packaging material etc.

In embodiments, pharmaceutical agents described herein may be formulated for oral administration. Agents described herein may be formulated by combining the active agent with, e.g., pharmaceutically acceptable excipients. In various embodiments, the agents described herein may be formulated in oral dosage forms that include, by way of example only, tablets, powders, pills, effervescents, capsules, liquids, gels, syrups, elixirs, slurries, suspensions, or other dosage forms like creams, ointments, implants, inserts, microneedles and the like.

The nanoparticles described herein may be used to prepare therapeutic pharmaceutical compositions. The nanoparticles may be added to the compositions in the form of an aqueous dispersion or as a dry powder of lyophilized nanoparticles. The nanoparticles may be formulated as pharmaceutical compositions and administered to a mammalian host, such as a human patient, in a variety of forms. The forms can be specifically adapted to a chosen route of administration, such as parenteral, topical, transdermal or oral administration.

The nanoparticles may be used in a variety of in vivo, ex vivo or in vitro diagnostic or therapeutic applications. Some examples are the treatment of diseases such as cancer, autoimmune disease, genetic defects, central nervous system disorders, infectious diseases and cardiac disorders, diagnostic uses such as radioimmunossays, PCR, enzyme linked immunoadsorbent assays, contrast imaging, immunoscintography, and delivering pesticides, such as herbicides, fungicides, repellants, antiviral, antimicrobials or other toxins. Non-genetic materials are also included such as growth factors, antibodies, hormones, chemokines, cytokines, interleukins, interferons, tumor necrosis factor, granulocyte colony stimulating factor, and other protein or fragments of any of these.

The present teachings are illustrated by the following examples.

EXAMPLES

Materials

Organosolv lignin was obtained from GreenValue S.A (Orbe, Switzerland). Curcumin, calcein AM and diamidino-2-phenylindole (DAPI) were purchased from Sigma-Aldrich Company (St. Louis Mo., USA). Anhydrous citric acid and trisodium citrate dihydrate were obtained from Acros Organics (Fisher Scientific). Tween 80, sodium azide and Dulbecco's Modified Eagle Medium were purchased from Fisher Scientific (Bridgewater, N.J., USA). Dialysis membrane (MWCO 8 kDa) was purchased from Spectrapor (Houston, Tex., USA). Citric acid monohydrate, dichloromethane, and ethanol were purchased from Merck (Darmstadt, Germany). Bovine serum albumin (BSA), HEPES, glucose, sodium chloride, potassium chloride, calcium chloride, magnesium chloride, sodium phosphate monobasic, potassium phosphate dibasic, sodium hydroxide, hydrochloric acid, formic acid, Hanks' Balanced Salt Solution (HBSS), and Lucifer yellow were purchased from Thermo Fisher Scientific (Waltham, Mass., USA). All solvents and chemical reagents were of analytical grade.

Example 1

Preparation of Curcumin-Loaded Lignin Nanoparticles

The Cur-loaded LG-NPs were prepared using a modified phase separation method. First, 40 mg of lignin (LG) was dissolved in 70% ethanol containing 2 mg of curcumin (CUR). The alcoholic phase was added dropwise under probe sonication to an aqueous phase consisting of 0.1M citrate buffer containing sodium citrate as stabilizer. The resulting colloidal dispersion was placed on a magnetic stirrer (300 rpm) for three hours to evaporate the ethanol.

The crosslinked nanoparticles were separated using Millipore centrifugal filters (molecular weight cutoff 8000 g/mol) and washed several times with deionized water to remove the free CUR. The filtrate was then dried using freeze-drying or spray-drying. The dried formulations were stored in a desiccator at 4° C. for further use. Optimization of the nanoparticle formulations was achieved by changing various formulation parameters such as the percentage of ethanol solvent, lignin concentration, or the curcumin to lignin polymer ratio.

Example 2

Characterization of the Lignin Nanoparticles

The mean particle size (expressed as hydrodynamic diameter—Dh), size distribution (expressed as polydispersity index—PDI), and zeta potential (expressed as mV) were determined using a Malvern Zetasizer-S 3600 (Malvern Instruments Inc., Southborough, Mass.). Each sample was measured in triplicate, and the results are expressed in Table 2 as mean±SD. For morphological analysis, the nanoparticles were visualized by scanning electron microscopy (SEM) and transmission electron microscopy (TEM) (FIGS. 2 and 3, respectively).

For the SEM study, 10 µL of nanoparticle dispersion was diluted and placed on a carbon coated slip sputtered with a thin layer of gold under an argon atmosphere prior to imaging using Field Emission Electron Microscope JEOL JSM-7600F (JEOL Ltd, Tokyo, Japan). For the TEM study, images were obtained using a JEOL JSM-2100F electron microscope (JEOL Ltd, Tokyo, Japan) operated at an accelerating voltage of 200 kV. The specimens were prepared by placing a dilute dispersion of the nanoparticles onto carbon-coated copper grids. Images analysis was performed using JEOL PC-SEM/TEM (version 2.1) software.

Example 3

Thermal and Fourier Transform Infrared Spectroscopy (FTIR) Analysis

The thermal behavior of the curcumin-loaded lignin nanoparticles formulation was studied using differential scanning calorimetry (DSC), using a DSC 8000 (PerkinElmer, Shelton, Conn., USA). The analysis was performed in conventional (i.e., heating only) mode. The samples were equilibrated at 0.0° C. with a modulation of +1.0° C. every 60 seconds, and isothermal heating for 5 minutes. The temperature was increased to 400.0° C.; the rate of increase in temperature was a ramp of 10.0° C./min. Analyses of the scans, including determination of glass transition (Tg) was performed using TA Instruments Universal Analysis software (TA Instruments, New Castle, Del.).

The chemical crosslinking interaction between citric acid and the lignin nanoparticles was examined using Fourier-Transform Infrared Spectroscopy (FT-IR). The IR spectra of citric acid, lignin powder, and citric acid-crosslinked lignin nanoparticles were recorded using an FT-IR spectrophotometer (ALPHA II ATR-FTIR, Bruker, USA). Results for lignin powder and CA cross-linked LG NPs are provided in FIG. 6.

Example 4

Influence of pH and Ionic Strength on LG NPS s Stability

To determine the effect of pH on nanoparticle size and zeta potential, the nanoparticles were dispersed in solution varying in pH from 2 to 10. The pH was adjusted using 0.1 M HCl or 0.1 M NaOH. Similarly, the effect of salt concentrations (0-200 mM of NaCl) on particle size and zeta potential of the nanoparticles was also determined (Tables 3 and 4). The nanoparticle size grew as pH decreased, especially for pH ranging from 2-6. As might be expected, the PDI was less variable.

Example 5

Determination of Loading and Encapsulation Efficiency

Quantitative analysis of CUR concentrations in the nanoparticles was performed by measuring the absorbance of CUR using a UV-Visible spectrophotometer (JASCO, Japan) at a wavelength of 420 nm. A calibration curve, generated by serial dilution of the stock solution, was used to determine CUR concentrations in unknown samples. Data were corrected by subtraction of the corresponding blank signal.

In particular, 2 mg of CUR-loaded nanoparticles was dispersed in deionized water and then centrifuged at 14000 rpm for 10 minutes. The supernatant was discarded and the pellet was dissolved in 50% hydroalcoholic solution. The CUR concentration was determined using a calibration curve in the range of 0.2 to 10 µg/ml of CUR in 50% alcohol. The CUR loading and CUR encapsulation efficiency were calculated as follows:

CUR Loading (%)=(Weight of CUR in Nanoparticles)/(Weight of Nanoparticles)×100

CUR Encapsulation Efficiency (%)=(Weight of CUR in Nanoparticles)/(Weight of initially added CUR)×100

Example 6

Solid State Stability and Photostability

For solid state stability and photostability of CUR loaded nanoparticles, 2 mg of curcumin, or the curcumin equivalent of CUR-loaded LG NPs, was kept in a sealed glass vial and placed in a stability chamber (Binder, Germany) at 25° C., 60% RH, or at refrigerator temperature 4° C., in the light or dark condition. At different time points Particle Size, PDI, zeta potential and CUR content were monitored for a period of 3 months. Stability was characterized by changes in particle size distribution and percent CUR remaining in the nanoparticles.

Example 7

In Vitro Release Studies

A quantity of 5 mg of Curcumin-loaded LG NPs was suspended in a phosphate-buffered solution under different pH conditions (pH 2 and pH 7.4), and placed in a water bath shaker (120 rpm) at 37° C. At predetermined time intervals, 1 ml supernatant aliquots were withdrawn and replaced by fresh buffer while maintaining the sink condition using 0.5% (w/v) Tween 80. The concentration of CUR released was monitored by reversed-phase HPLC system using Phenomenex Luna C18 (250 mm×4.6 mm, 5 µm) on Shimadzu HPLC system (Tokyo, Japan). The mobile phase was composed of acetonitrile and citric acid (60:40 v/v) at a flow rate of 1 mL/min and the effluent was monitored at 420 nm (Ma, Shayeganpour, Brocks, Lavasanifar, & Samuel, 2007). The curcumin concentration was determined using the standard curve obtained for known concentrations of curcumin. The curve was found to be linear in the concentration range 0.002-5.00 µg/mL. The lower limit of quantification was 5 ng/mL, which can be detected with good accuracy and precision. Each sample of nanoparticles was analyzed in triplicate and the results expressed as mean±SD.

Example 8

Cell Culture

Differentiated Caco-2 cells (ATCC, Rockville, Md., USA) were maintained in DMEM (4.5 g/L glucose) medium supplemented with 20% FBS (HyClone; Thermo Scientific, Waltham, Mass., USA), 1% non-essential amino acids, 1% L-glutamine, 1% streptomycin (100 µg/ml) and penicillin (100 IU/ml). The growth medium was changed every day in the first two weeks followed by three times a week.

Example 9

MTT Assay and Evaluation of Caco-2 Cell Monolayer Integrity

The cell viability of unloaded LG NPs, CUR-loaded LG NPs, and free CUR was evaluated against Caco-2 cells lines to assess the toxicity of formulations in comparison to the free CUR, using the colorimetric 3-(4, 5-dimethylthiazol-2-yl)-2,5-diphenyltetrazolium bromide (MTT) assay. Caco-2 cell line was transferred into 96-well plates, at a density of 5×104 cells per well. After cell adhesion, the culture media was removed and the cells were incubated with 250 µL of culture media containing a concentration range from 10 µM to 300 µM of CUR as free, CUR loaded LG NPs and equivalent unloaded LG NPs.

For free CUR, the samples were prepared from a stock solution in DMSO with appropriate dilutions to reach a maximum of 2% (v/v) of DMSO in each well. After a 24 h incubation period, the supernatant was removed and replaced by 100 µL of MTT solution (0.5 mg/ml) at (37 C°, 5% CO2) to allow MTT to be metabolized. After 2 h incubation, the MTT solution was removed and 100 µL of DMSO was added into each well to solubilize formazan (metabolic product of MTT). Optical density was read at a wavelength of 570 nm using a microplate reader (ELX 800, Bio-Tek Instruments, Winooski, Vt., USA).

The induced cytotoxicity was calculated by comparing the optical density (OD) values against control wells. Cytotoxicity was expressed as IC50-value which was calculated as the concentration of the sample inhibiting cell viability by 50%. Cell viability of more than 80% was considered as nontoxic. For LG NPs experiments cells treated with 4% (v/v) DMSO were used as negative control for free CUR. All measurements were performed in triplicate and the means±standard deviation (SD) were calculated. The results are provided in FIG. 9.

For evaluation of Caco-2 cell monolayer integrity the assay was done by analyzing the concentration of lucifer yellow (LY) in the apical and basolateral compartments. A working concentration of LY (100 µM) was prepared from stock solution. The LY was then added to the apical side of Caco-2 cell monolayer using 6-well Transwell inserts (Corning Transwell Clear, pore size 0.4 µm) at a cell density of 106 cells per cm. Equal amount of HBSS buffer (pH 7.4) was added to the basolateral side. The plate was then kept in a shaker incubator at 37° C. After different time points, 200 µl of the samples were withdrawn from the basolateral side and apical side. The samples were analyzed by fluorescence spectroscopy at an excitation wavelength of 485 nm and emission wavelength of 535 nm using spectrofluorimetry (JASCO FP-8300, JASCO, Japan). Results are provided in FIG. 11.

In addition, Transepithelial electrical resistance (TEER) was measured using an EVOM meter (World Precision Instruments, Inc., Sarasota, Fla.) equipped with a pair of chopstick electrodes. The electrode tip was balanced with HBSS buffer overnight in sterile condition before measurement. TEER was calculated as following:

$$\text{TEER } (\Omega \cdot cm2) = (R \text{ total} - R \text{ filter}) \times A$$

where R ($\Omega$) is the measured resistance, and A is the surface area ($cm^2$). Calcium-free HBSS containing 5 mM EDTA was used as a positive control. The TEER of the Caco-2 cell monolayers was measured throughout 6 hours incubation period. Results are provided in FIG. 10.

Example 10

In-Vitro Transepithelial Transport and Uptake of Nanoparticles

Caco-2 cells were seeded at 1×106 cells onto Transwell polyester filter membranes (pore size 0.4 µm, growth area 4.67 cm2) using 6-well sterile plates (Transwell®, Corning Costar Corp., Cambridge, Mass., USA). The cells were grown in an atmosphere of 5% $CO_2$, 95% relative humidity, with the temperature at 37° C. The cells were maintained in FBS-supplemented DMEM, and the culture medium was added to both apical and basolateral compartments, with replacement every two days, during 23 days, until the monolayer achieved minimum of 400 $\Omega$ cm2 of transepithelial electrical resistance (TEER) values.

For the permeability study, the cell monolayers were rinsed twice with HBSS salt solution, at pH 6.5, and equilibrated under experimental conditions for 20 minutes. An aliquot (500 µl) of free CUR in THFP (Glycofurol/Ethanol) (80/20) (v/v), or in a CUR-loaded LG NPs dispersion containing an equivalent amount of 50 µM of CUR, was applied to the apical side of the monolayer. The monolayers were then incubated at 37° C. under controlled atmosphere (5% CO2, 95% relative humidity) with continuous agitation. The permeability of free CUR or CUR-loaded LG NPs was determined for 6 hours. Aliquots were withdrawn from the basolateral compartment at pre-determined time points and replaced with fresh buffer solution. The apparent permeability coefficient (Papp) was calculated using the following equation $$\text{Papp (cm/s)} = [(dQ/dt)/(1/A \cdot C0)] \times 100$$

Where dQ/dt is the flux of CUR across the Caco-2 monolayer; C0 is the initial concentration of CUR in the apical chamber; and A is the surface area of the filter (4.67 $cm^2$). The results provided in FIG. 12.

Example 11

Caco-2-Uptake

A Caco-2 uptake assay procedure was performed according to a standard method, as follows. After 80% cell confluence, the medium was removed and washed with HBSS. The cells were then incubated with a free CUR solution, or with CUR-loaded LG NPs in the HBSS for a range of different time points. At the end of the incubation periods, the cell monolayer was rinsed three times with cold PBS to remove excess nanoparticles. To visualize the nucleus of the cells, the cells were stained with DAPI. Following that, the cells were imaged under a confocal laser scanning microscope (Carl Zeiss LSM 410, Goettingen, Germany) using a 100× oil immersion objective lens and DAPI/FITC filters. The images were then processed with the aid of Carl Zeiss LSM software. The results showed that the nanoparticles were mostly entering the cells.

Example 12

P-Gp Inhibition (Calcein AM Assay)

Caco-2 cells were seeded in black 96-well plates overnight at a density of $2 \times 10^5$ cells/ml. The following day, the cells were treated with 50 µL of blank nanoparticles diluted in PBS buffer for 30 minutes. The cells were the washed three times, followed by addition of calcein AM (Molecular Probes) at a concentration of 0.5 µM to a final volume of 200 µl/well at 37° C. The cells were washed two times with ice-cold PBS, and lysed with 0.5% Triton-X100/PBS.

Blank buffer solution was used as control. The uptake of calcein was measured at 485 excitation and 530 emission wavelengths using spectrofluorimetry (JASCO FP-8300, JASCO, Japan). To determine P-gp inhibition, the relative calcein fluorescence intensity was calculated for the LG NPs treated and non-treated groups using the following equation:

$$\% \text{ Relative Fluorescence} = [(FL(\text{treatment}) - FL(\text{non-treated}))/(FL(\text{non-treated}))] \times 100$$

Example 13

Pharmacokinetics Analysis

Male Sprague Dawley rats (250-300 g) were acquired from (Animal Care and Use Centre, King Saud University, Riyadh, Saudi Arabia). All procedures were approved by the Animal Care and use committee of King Saud University and performed according to NIH guidelines.

The rats were housed under normal conditions with free access to food and water and kept on a 12-h light/dark cycle. Rats that received oral administration were fasted overnight before the study, and no food was provided up to 6 hours after oral gavage. For the CUR pharmacokinetic study, the rats were divided at random into three groups with 8 animals in each group. Before dosing, 200 µL of blood were taken from the retro-orbital plexus of the rats as blank samples, and transferred into heparinized Eppendorf tubes.

The first group of rats each received an intravenous dose of CUR (10 mg/kg) diluted with saline, injected into the tail vein. The other two groups of animals received oral CUR, either as a CUR suspension in CMC, or as CUR-loaded LG NPs formulation dispersed in water (equivalent to 50 mg/kg). Following administration by oral gavage, blood samples of 200 µl were withdrawn from the retro-orbital plexus at different time points (0, 0.25, 0.5, 1, 2, 4, 6, 8, 12, 24, and 48 hours) into 1 ml heparinized blood collection tubes. The samples were centrifuged for 15 minutes at 14000 rpm. Then, the plasma was collected and stored at −80° C. until further analysis was conducted by RP-HPLC.

Each Aliquot (50 µL) of sample plasma was added to 100 µL of acetonitrile to denature CUR-binding proteins, usually by precipitation, before extraction. The CUR in the resulting samples was extracted via a liquid-liquid extraction using a mixture of 50:50 Ethyl Acetate-Hexane, and then evaporated to remove the organic solvent under a dry nitrogen atmosphere. The dry extract was dissolved in ethanol, and then subjected to reverse-phase HPLC.

For the pharmacokinetics analysis, a non-compartmental analysis of CUR plasma concentrations was performed using PK Solutions 2.0 software (Summit Research Services, Montrose, Colo., USA). The data were represented by the following parameters: area under the curve (AUC) was calculated by the trapezoidal method from zero to the final sampling time; plasma half-life (t1/2); peak concentration (Cmax); and time of peak concentration (tmax). Absolute bioavailability (Fabs), which compares the bioavailability of CUR in the systemic circulation following oral administration with intravenous injection, was calculated according to the following formula:

$$Fabs(\%) = \frac{AUCPO.dose\text{-}iv}{AUCiv.dose\text{-}PO} \times 100$$

Relative bioavailability (Frel) measures the bioavailability (estimated as the AUC) of CUR-loaded nanoparticles when compared with CUR suspension following oral administration. Relative bioavailability (Frel) was calculated at the same dose by using the following formula:

$$Frel(\%) = \frac{AUCnanoparticles}{AUCsuspension} \times 100$$

All the experiments were conducted in triplicate. Data is represented as the mean±standard deviation. Statistical evaluation was performed by Student's t-test and analysis of variance (ANOVA) using Minitab® statistical software (Minitab Inc., State College, Pa.) at a significance level of p <0.05.

Example 14

In Vitro Release Studies

The in-vitro release of CUR from the nanoparticles was tested in simulated gastric fluid (SGF) and in simulated intestinal fluids (SIF). Orally-administered nanoparticles encounter both SGF and SIF before the curcumin was fully absorption. The results showed that 8.7% of CUR was released in SGF after 4 hours. However, the release rate was increased and sustained in SIF.

Figure 7:
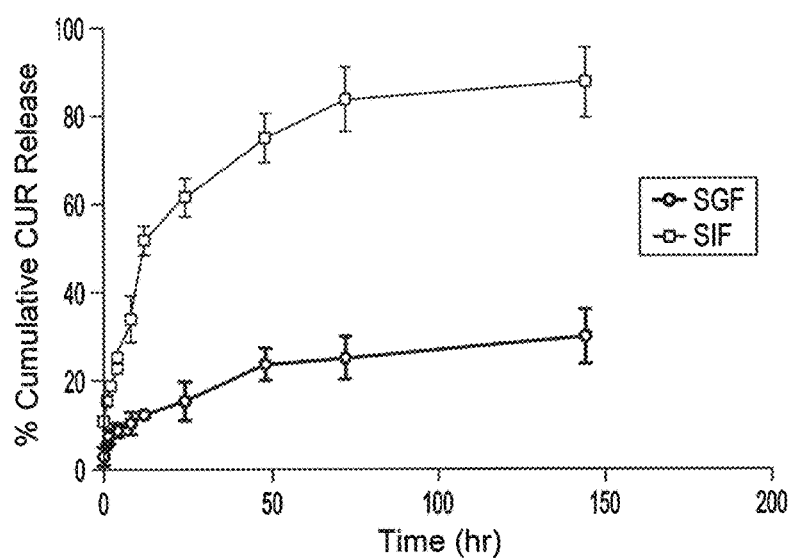
FIG. 7 is a graph reflecting the cumulative percent of curcumin release from LG NPs in simulated gastric fluid (SGF) and simulated intestinal fluid (SIF). Each data point represents mean±SD; n=3.

LG NPs were able to retard the CUR release at the relatively harsh acidic medium encountered in the stomach. This is thought to be due to lignin crosslinking, or to the swelling that occurs at low pH, as well as the quick erosion of the particles at the higher pH level. Results are provided in FIG. 7.

Lignin diffusion may decrease when exposed to acidic pH because of formation of hydrogen bonds between the carboxy-methyl groups, due to the existence of carboxylic groups at low pH. At higher pH, the larger swelling force caused by the electrostatic repulsion between the ionized groups may result in a greater release/diffusion of the CUR. This is important criteria for delivering drugs or macromolecules which can easily decompose in acidic media.

CUR release in aqueous media was sustained for up to 6 days. The CUR release profile from the LG NPs was low and sustained under acidic conditions, and reached about 34% of CUR release by the end of an 8-hour period of time under intestinal conditions (i.e., higher pH). In reality, the remaining content of CUR loaded within the LG NPs will either be absorbed by the intestinal epithelial cells, or released as the LG NPs traverse the intestinal lumen.

As is well known in the industry, drug release from a polymeric matrix depends mainly on the degradation rate of the polymer chains. In contrast, the CA cross-linker may play a role in restricting the mobility and hydration in the lignin matrix. As a result, using a CA cross-linker may change the ionic structure, mechanical strength, swelling properties, and degradation rate of the lignin. These factors, along with the specific crosslinking of the lignin polymer and the relative binding affinity of the CUR, all may affect the release rate and release extent of the CUR.

Example 15

In Vitro Evaluation of LG-NPs

The LG NPs provide enhanced oral delivery of CUR. In general, intestinal drug absorption depends on several factors, such as the drug solubility, stability with regard to the enzymes present in the gut mucosa, and the presence of efflux transporters, which are involved in expulsion of some drug molecules. The Caco-2 cell line expresses morphological characteristics similar to small intestine cells, such as tight intercellular junctions, microvilli, and a number of enzymes and transporters. Thus, this cell line was used as a model to mimic intestinal cell types.

Figure 8:
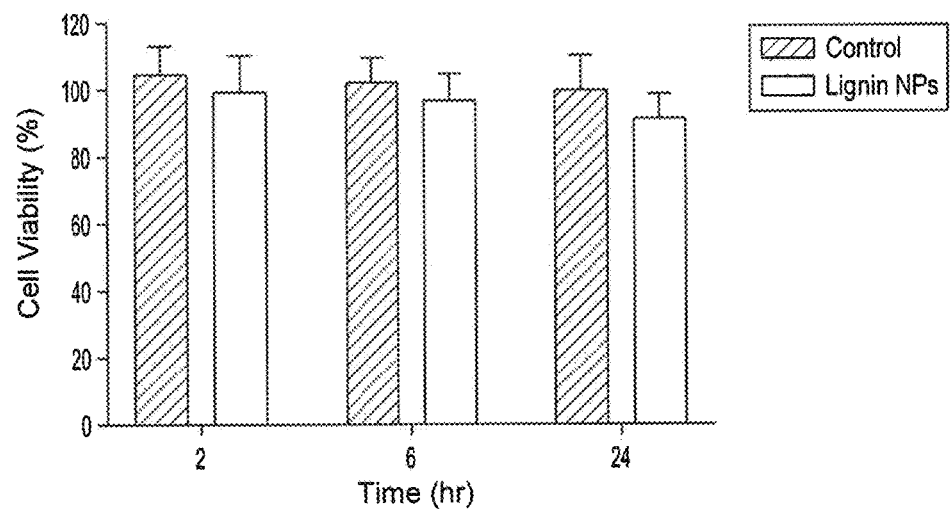
FIG. 8 is a graph reflecting cell viability of caco-2 cells exposed to LG NPs for 2, 6, and 24 hours. Data is expressed as the mean±SD; n=3.

An MTT assay was used to evaluate the biocompatibility of LG NPs, and to choose an optimum concentration that would have no effect on cell viability during the course of in vitro permeation studies. Caco-2 cells treated with blank LG NPs maintained cell viability above 80%, with no statistical differences from the untreated cells (FIG. 8).

Figure 9:
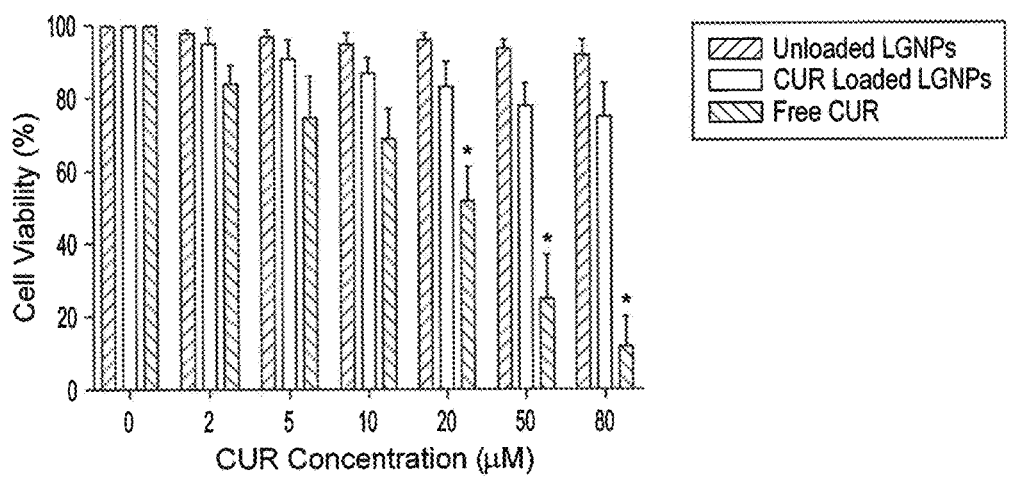
FIG. 9 is a graph reflecting cell viability of Caco-2 cells after incubation for 24 hours at 37° C. as follows: CUR concentrations of 0, 2, 5, 10, 20, 50, and 80 μM, with each of (1) blank NPs, curcumin-loaded nanoparticles, and free curcumin, as assessed by the MTT assay. Data is expressed as the mean±SD; n=3.

The studies were conducted with unloaded LG NPs, CUR-loaded LG NPs, and free CUR, at CUR concentrations ranging from 0 to 80 µM (FIG. 9). At high free curcumin concentrations tested (50 µM and 80 µM), the cell viability was below 50%. In contrast, at this concentration all CUR-loaded LG NPs concentrations exhibited cell viability of more than 80% —indicating no cytotoxicity. As a result, a working concentration of (50 µM) was selected for further permeation studies. Previous reports indicated that CUR loaded at such concentrations showed no cytotoxicity after 72-h incubation. The cellular uptake of CUR loaded LG NPs was confirmed by confocal microscopy.

Figure 10:
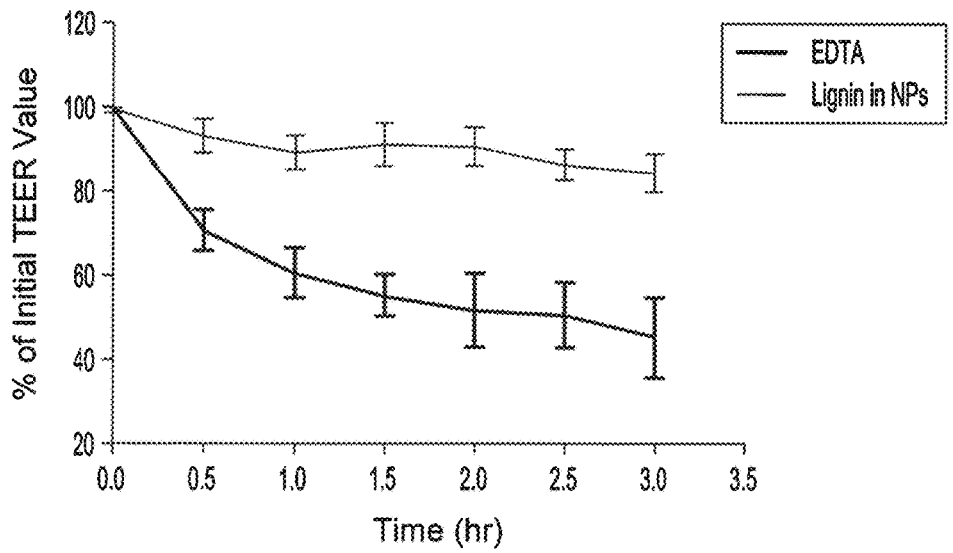
FIG. 10 is a graph reflecting the effects of nanoparticles (2 mg/ml) and EDTA (5 mM) on the transepithelial electrical resistance (TEER) in Caco-2 cell monolayers. Data is expressed as the mean±SD; n=3.

Monolayer integrity was monitored by measuring the trans-epithelial electrical resistance (TEER) with a voltmeter. A TEER value of (>800 ohm/sq.cm) was maintained (FIG. 10). This demonstrated that the Caco-2 cells had formed a proper monolayer with efficient, tight junctions that allowed the passage of the drugs by the transcellular route.

Figure 11:
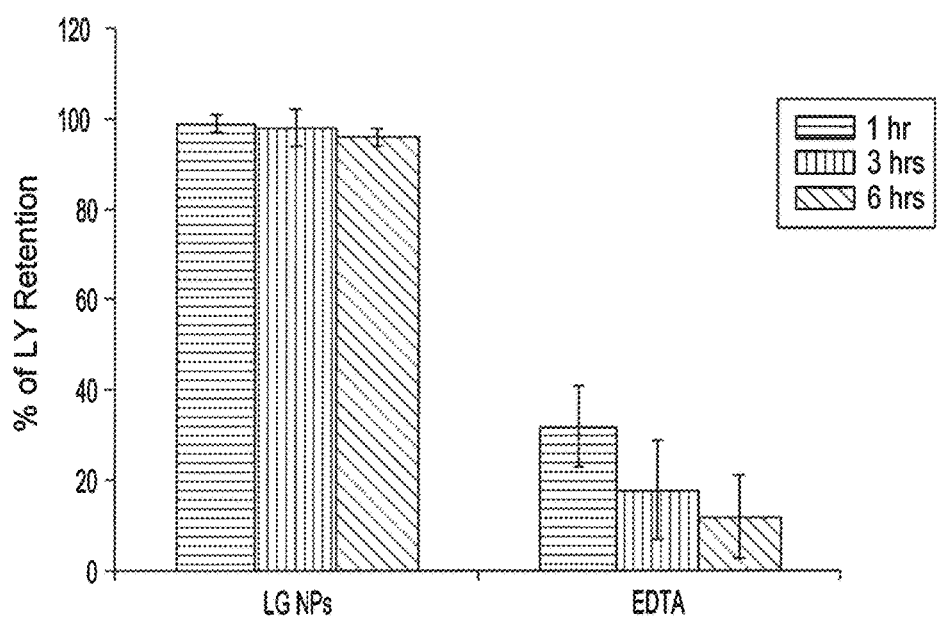
FIG. 11 is a graph reflecting the effect of nanoparticles (2 mg/ml) and EDTA (5 mM) on the Lucifer yellow (LY) retention in Caco-2 cell monolayers. Data is expressed as the mean±SD; n=3.

Another validation for monolayer formation was performed by the permeability experiments for the fluorescent dye (Lucifer Yellow) (FIG. 11). The rejection rate of LG NPs was more than 90%, compared with the positive control (EDTA) after 6 hour experiment. This further confirmed the validity of the protocol used for the monolayer formation.

Figure 12:
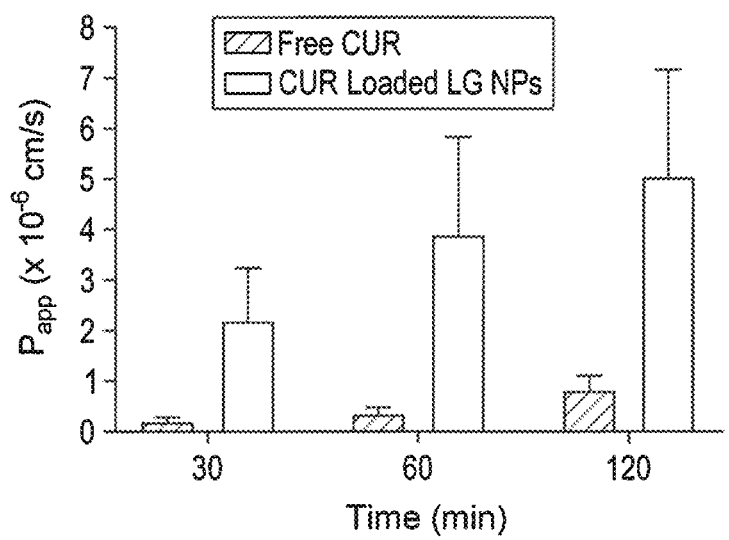
FIG. 12 is a bar chart reflecting the apparent permeability (Papp) coefficients of free curcumin and CUR-loaded LG NPs in Caco-2 monolayers. Data is expressed as the mean±SD; n=4.

Previously, it was known that curcumin has poor permeability in the in-vitro Caco-2 model system (Papp <3.18× 10-6 cm/s). Bi-directional transport of CUR was examined to assess the permeability of free CUR, compared to CUR-loaded LG NPs, across a Caco-2 cell monolayer cultured in Transwell chambers (FIG. 12). The results show the time profiles of trans-epithelial transport of free CUR and CUR-loaded LG NPs across Caco-2 cell monolayers.

Apparent permeability coefficients were calculated for free CUR and CUR-loaded LG NPs. The nanoparticles showed an enhancement of CUR permeation by the LG NPs as compared to the free CUR at all-time points. The apparent permeability coefficient of CUR was found to be about 5× greater when loaded in the nanoparticles. These results, along with the release profile of CUR, may be linked to the nanoparticle uptake by the intestinal cells.

In similar studies, the transcellular bypass of PLGA nanoparticles by intestinal cells has been reported. Such phenomenon may lead to improved bioavailability of CUR after oral administration. In contrast, efflux pumps expressed in the intestinal cells can limit curcumin absorption. Previous studies have suggested that polyethylene glycols and their derivatives (e.g. TPGS-1000) can inhibit the function of P-gp by changing the membrane fluidity, thereby improving the intestinal absorption of P-gp substrates, which are secreted by a P-gp-mediated efflux system.

Figure 13:
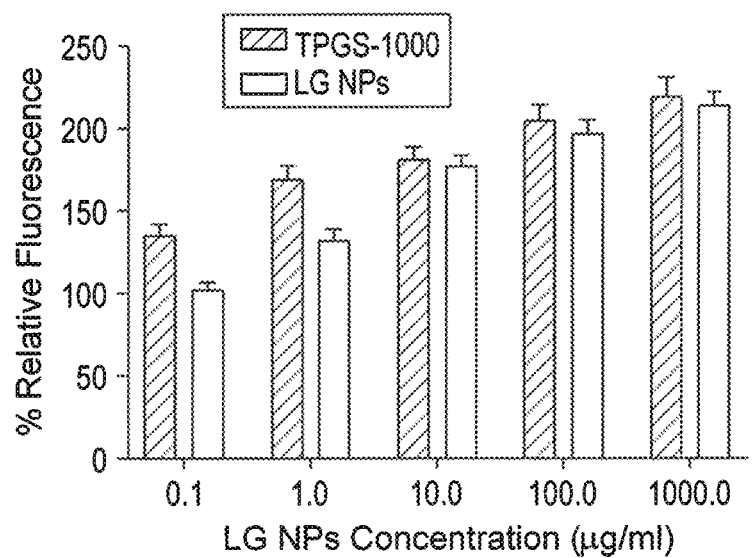
FIG. 13 is a bar chart reflecting the effect of different concentrations of LG NPs on calcein-AM uptake by Caco-2 cells. The Y-axis represents percent relative fluorescence of 0.5 μM calcein-AM compared to untreated control TPGS-1000 (tocopheryl polyethylene glycol 1000-succinate) after 30 min incubation with LG NPs at concentrations of 0.1, 1.0, 10.0, 100.0, and 1000.0 μg/ml. Data is expressed as the mean±SD; n=4.

Here, calcein AM, a P-gp substrate, was used to study the P-gp inhibitory activity of the LG NPs. Lignin demonstrates a concentration-dependent P-gp inhibitory effect comparable to the positive control, TPGS-1000 (FIG. 13). The significant reduction in the efflux ratio of our prepared LG NPs may suggest that CUR-loaded LG NPs bypassed the P-gp efflux and thus enhanced CUR permeability. However, further studies are required to understand the mechanism of inhibition of P-gp efflux by lignin. Overall, the results suggest that the LG NPs enhanced intestinal permeability of CUR.

Example 16

In Vivo Pharmacokinetics

As discussed above, while CUR is reported to provide health benefits, one of the major limitations with orally-administered CUR is its poor oral bioavailability. This is due to low solubility, poor absorption, excess metabolism, and rapid systemic elimination from the patient's body. The data of a prior pharmacokinetics study showed that a maximum plasma concentration of 0.06±0.01 µg/mL was reached for orally administered CUR, while a maximum blood serum concentration of 0.36±0.05 µg/mL was the result of i.v. administration. The oral bioavailability of curcumin was only 1%.

Figure 14:
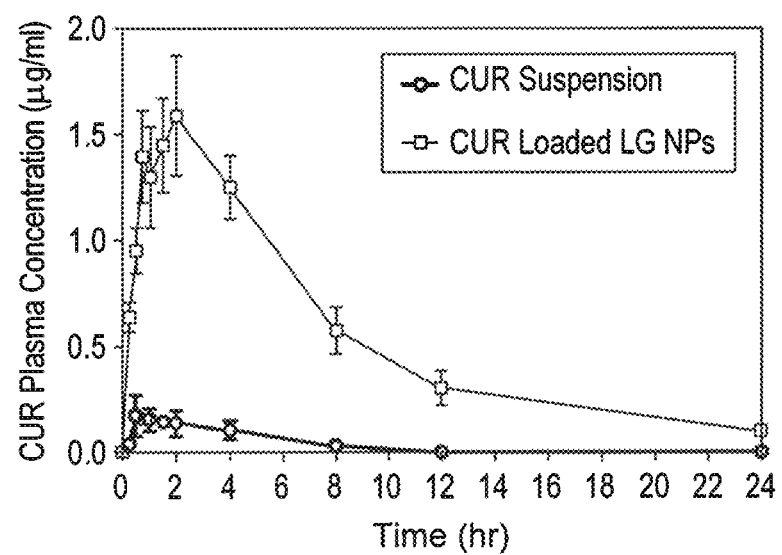
FIG. 14 is a graph reflecting the plasma concentration profiles of curcumin for 24 hours after oral administration of either curcumin suspension, or curcumin-loaded lignin nanoparticles. Data is expressed as the mean±SD; n=4.

Polymeric nanoparticles have received a lot of attention due to their ability to enhance drug solubility and stability. To evaluate and compare the pharmacokinetics of the present CUR formulations when delivered orally, we treated rats with oral doses of the CUR-loaded LG NPs formulation, compared to plain CUR suspension. The resulting plasma concentration-time profiles and PK parameters are presented in FIG. 14 and in Table 5. Table 5 provides pharmacokinetic parameters of CUR after oral administration into healthy rats, comparing CUR—curcumin; LG NPS s—lignin nanoparticles; and CMC—carboxymethyl cellulose.

TABLE 5

Pharmacokinetic parameters of CUR after oral administration into healthy rats

| PK Parameters | CUR Formulations | |
|---|---|---|
| | Oral CMC suspension | Oral CUR loaded LG NPS s |
| Dose (mg kg$^{-1}$) | 50 | 50 |
| T$_{max}$ (h) | 0.49 ± 0.18 | 1.98 ± 0.69 |
| C$_{max}$ (µg ml$^{-1}$) | 0.172 ± 0.09 | 1.58 ± 0.21 |
| t$_{1/2}$ (h) | 3.40 ± 1.39 | 8.97 ± 1.22 |
| CL (L· h$^{-1}$) | 56.32 ± 4.65 | 3.58 ± 0.12 |
| AUC$_{0-\infty}$ (µg · h · ml$^{-1}$) | 2.215 ± 0.63 | 14.115 ± 1.516 |
| MRT (h) | 2.53 ± 0.414 | 8.89 ± 0.587 |
| F$_{abs}$ (%) | 1.65 | 22.58 |
| F$_{rel}$ (%) | — | 637.47 |

C$_{max}$ = the maximum observed concentration.
T$_{max}$ = the time at maximum observed concentration.
t$_{1/2}$ = the time for concentration to reduce by one-half in the elimination phase.
AUC$_\infty$ = the total area under the curve calculated using observed data points combined with an extrapolated value.
K$_a$ = absorption rate constant.
K$_e$ = elimination rate constant.
MRT = first-order moment mean residence time.
F$_{abs}$ = absolute bioavailability.
F$_{rel}$ = relative bioavailability.

The CUR suspension showed Cmax of 0.172±0.09 µg/mL at 1.59 hours (Tmax) post administration, with the AUC$_0$-∞ value of 2.415±0.93 µg·h/ml. The absolute bioavailability of 2.65% demonstrated the distinctive limitations of the oral administration of CUR. In stark contrast, administration of CUR-loaded LG NPs resulted in a significantly higher Cmax value of 1.58±0.21 µg/ml, at Tmax of 2 hours, with an AUC0-∞ value of 16.115±1.52 h µg/mL.

The AUC$_0$-∞ following administration of CUR-loaded LG NPs was around 7× greater than that for the free CUR in suspension form. This much-larger AUC suggests that CA cross-linked LG NPs could protect CUR from degradation while in the GI tract. The resulting significant increase in mean residence time (MRT) compared to the CUR suspension was observed, likely due to the sustained release of CUR from the LG NPs as demonstrated in the in vitro release studies.

CUR-loaded LG NPs also exhibited a longer elimination half-life (9 hours) compared to the CUR suspension, confirming the prolonged drug residence provided by the LG NPs following oral administration, and the longer absorption of CUR in the GI tract. The relative bioavailability of CUR-loaded LG NPs to the suspension was about a 5.7× increase.

It is to be understood that the method of synthesizing lignin-based nanocompositions is not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A method of synthesizing lignin-based nanoparticles, consisting of the steps of:

dissolving lignin in a solvent to form an alcoholic phase, the solvent including ethanol and curcumin;

adding the alcoholic phase to an aqueous phase, wherein the alcoholic phase is added dropwise to the aqueous phase under probe sonication, further including a citrate buffer to form a colloidal dispersion, wherein the citrate buffer includes sodium citrate as stabilizer; and evaporating the ethanol from the colloidal dispersion to prepare a dried formulation including the nanoparticles, wherein the lignin concentration is less than 0.4% w/v and the nanoparticles have a mean particle size diameter of less than 100 nm and a distribution of less than about 0.116.

* * * * *